(12) United States Patent
Yen

(10) Patent No.: US 9,351,925 B2
(45) Date of Patent: *May 31, 2016

(54) SUBMICRON PARTICLES TO DECREASE TRANSFUSION

(76) Inventor: Richard C. K. Yen, Yorba Linda, CA (US)

( * ) Notice: Subject to any disclaimer, the term of this patent is extended or adjusted under 35 U.S.C. 154(b) by 560 days.

This patent is subject to a terminal disclaimer.

(21) Appl. No.: 13/604,770

(22) Filed: Sep. 6, 2012

(65) Prior Publication Data

US 2013/0064864 A1    Mar. 14, 2013

Related U.S. Application Data

(60) Provisional application No. 61/573,630, filed on Sep. 10, 2011, provisional application No. 61/627,623, filed on Oct. 14, 2011.

(51) Int. Cl.

| | | |
|---|---|---|
| *A61K 9/14* | (2006.01) | |
| *A61P 7/02* | (2006.01) | |
| *A61K 38/38* | (2006.01) | |
| *A61K 9/00* | (2006.01) | |
| *A61K 38/36* | (2006.01) | |
| *A61K 9/50* | (2006.01) | |
| *A61K 9/51* | (2006.01) | |
| *A61K 9/10* | (2006.01) | |

(52) U.S. Cl.
CPC .............. *A61K 9/0019* (2013.01); *A61K 9/5052* (2013.01); *A61K 9/5169* (2013.01); *A61K 38/363* (2013.01); *A61K 9/10* (2013.01)

(58) Field of Classification Search
CPC ........... A61K 9/1658; A61K 47/48884; A61K 9/1611; A61K 9/1617; A61K 9/5169; A61K 47/48876; A61K 9/5192; A61K 38/363; A61K 47/42; A61K 47/488; A61K 9/1676; A61K 9/1682; A61K 9/1694; A61K 38/38
See application file for complete search history.

(56) References Cited

U.S. PATENT DOCUMENTS

| | | | |
|---|---|---|---|
| 6,262,019 B1 | 7/2001 | Keller et al. | |
| 6,916,795 B1 | 7/2005 | Youssef | |
| 2006/0258537 A1* | 11/2006 | Stella et al. | 504/291 |
| 2011/0189299 A1* | 8/2011 | Okubo et al. | 424/491 |
| 2011/0251127 A1* | 10/2011 | Yen | 514/13.7 |

OTHER PUBLICATIONS

Dr. Anrei Gudkov, Radiation Sickness Cures and Anti-Radiation Pills, http://nextbigfuture.com/2009/07/radiation-sickness-cures-and-anti.html, Jul. 20, 2009.

* cited by examiner

*Primary Examiner* — Audrea Buckley
(74) *Attorney, Agent, or Firm* — David A. Guerra

(57) ABSTRACT

A submicron protein sphere and method to intravenously treat a patient requiring blood component transfusion. The submicron protein spheres have a size ranging from 1.0 micron to less than 0.1 micron and a molecular weight ranging from 780 billion Daltons to less than 0.8 billion Daltons. The protein spheres have no biologically active molecules added or bound to the protein spheres prior to administering to the patient. The protein used to construct the spheres can be human serum albumin from natural sources or recombinant DNA-derived serum albumin, or other proteins such as gelatin or synthetic polypeptides. However, the protein spheres can bind the various clotting factors including fibrinogen after the spheres have entered the blood stream, binding the necessary additional biologically active molecules supplied in vivo from the patient's own blood, and possibly in vitro.

16 Claims, No Drawings

SUBMICRON PARTICLES TO DECREASE TRANSFUSION

CROSS-REFERENCE TO RELATED APPLICATION

This application is an U.S. non-provisional utility application under 35 U.S.C. §111(a) based upon U.S. provisional applications 61/573,630 filed on Sep. 10, 2011 and 61/627,623 filed on Oct. 14, 2011. Additionally, this U.S. non-provisional utility application claims the benefit of priority of U.S. provisional applications 61/573,630 filed on Sep. 10, 2011 and 61/627,623 filed on Oct. 14, 2011. The entire disclosures of the prior applications are incorporated herein by reference.

BACKGROUND OF THE INVENTION

1. Field of the Invention

The present invention relates to the field of blood component transfusion, specifically in a new method of treatment to decrease the need for transfusion such as red blood cell and platelet transfusion in human and animal patients. Transfusion of blood components can mitigate the morbidity in patients suffering from, for example, insufficient concentrations of red blood cells, white blood cells and platelets, in vivo, due to various causes. A new method of treatment to decrease the need for transfusion with natural blood components or to replace them is especially vital to the recovery of some patients who are particularly susceptible to the effects of radiation, burn or chemotherapy treatment.

2. Description of the Prior Art

Exposure to massive doses of ionizing radiation, such as after a dirty-bomb or atomic-bomb explosion, or a nuclear-reactor or medical radiation accident, can lead to major morbidity and/or mortality. If the victim survives the direct effect of the bomb blast, he still may suffer from damages to the nervous, digestive, pulmonary, hematopoietic and other vital systems. Published articles have revealed that transfusion of blood components, e.g. red blood cells and platelets can decrease the morbidity and mortality among irradiated patients. In these situations, blood components can be the main method of treatment without the concomitant use of other treatments, or the blood components can be used as an adjunct, to be used in conjunction with other treatments, such as those to be mentioned below. However, the infrastructures for the procurement, maintenance and distribution of blood components are not reliable during war times or when a national crisis has occurred.

One group of patients is particularly susceptible to the ill effects of agents that can lead to suboptimal concentrations of red blood cells, white blood cells and platelets in vivo, including agents such as irradiation, burn and chemotherapy. These are patients who are on anti-platelet treatment or anti-coagulation treatment for a variety of reasons. They will have excessive internal bleeding and increased morbidity and mortality compared to patients who are not on such anti-platelet or anti-coagulation treatments.

Various methods have been employed to treat radiation sickness, all with limited success. For example: (1) Neumune, an androstenediol, had been used by the US Armed Forces Radiobiology Research Institute under joint development with Hollis-Eden Pharmaceuticals; (2) A Chinese herbal medicine called Cordyceps sinensis had been used to try to protect the bone marrow and digestion systems of mice after whole body irradiation; (3) Bisphosphonate compounds had also been tried; (4) U.S. Pat. No. 6,916,795 disclosed an "energy-protective composition" comprising adenosine phosphates; (5) Garnett and Remo disclosed at the International Symposium on Application of Enzymes in Chemical and Biological Defense, Plenary Session Abstract, May 2001 that "DNA Reductase" had some "Opportunist Clinical Activity Against Radiation Sickness"; and (6) U.S. Pat. No. 6,262,019 disclosed a composition called MAXGXL which contains glytathione. All of the above are soluble enzymes, steroids or small molecules.

Of particular interest is the discussion listed under: http://nextbigfuture.com/2009/07/radiation-sickness-cures-and-anti.html It discussed:

(1) the effect of a small-molecule inhibitor to the p53-mediated apoptosis. A single shot of this drug, called CBLB502, at less than 1% of the maximum dose resulted in an 87% survival rate of mice exposed to an otherwise lethal dose of 13 Gray of radiation. By comparison, even at the maximum dose of the second-best chemical, called amifostine, only 54% of similarly irradiated mice survived.

(2) The work done at the Boston University School of Medicine on new compounds called the "EUK-400 series" which may be taken orally.

(3) DARPA funded work done at the Rice University called "Nanovector Trojan Horses, NTH." These carbon nanotube-based drugs may scavenge free radicals and mitigate the effects of ionizing radiation.

All of the above treatments employ mechanisms very different from the present invention. While some of the above mentioned treatments may result in improved survival of irradiated patients, it is not clear if the survivors will have other long-term medical problems caused by the irradiation or by the treatment. Therefore there is need for a new treatment that will improve survival, yet with less or no long-term medical problems among the survivors, caused either by the radiation or by the side-effects of the treatment.

In this application the term "improved survival" or "to improve survival" can mean: (1) a prolong survival time, e.g. if 100% of the irradiated subjects will die before day-30 without treatment, a treatment will be considered effective in prolonging life if it takes longer than 30 days (e.g. a year) before 100% of a similarly irradiated group dies (possibly from other problems); or (2) an increase in the survival rate at a fixed time (e.g. 30-day survival rate, or 90-day survival rate) after irradiation. Also the irradiation dose can be maximally lethal, leading to 100% of the irradiated subjects dying if untreated; or minimally lethal, having only, e.g. 5% of the irradiated subjects dying—both will be called "a lethal dose of irradiation."

While the above-mentioned prior-art treatment methods fulfill their respective, particular objectives, requirements and are aimed at improving survival of irradiated subjects, it is not clear that these treatments can result in fewer units of blood components being needed to support the patient during treatment. Therefore a new method of treatment is needed which can decrease the need for transfusion, whether in the frequency or in the amount of transfusion of blood components, whether the above-mentioned prior-art treatment methods were concomitantly used for the patient or not.

In addition, it would be most preferable that the new method of treatment will be able to improve survival all by itself without the use of any blood components or the use of any prior-art treatment for irradiated patients.

Moreover, it would be highly preferable that the new method of treatment will be able to decrease the morbidity of irradiated subjects all by itself without the use of any blood components or the use of any prior-art treatment for irradiated patients. Less morbid patients can assist themselves and use up less of the vital medical resources. Also, a patient that is not actively bleeding is more likely to receive help in a time of crisis than another one that is oozing blood.

The new method of treatment that can decrease the use of blood components will also be useful in cancer patients whose blood producing capacity is diminished, or patients receiving chemotherapy or radiation therapy, or any other medical, surgical, trauma patient in need of blood component therapy, including and not limited to red blood cell transfusion, platelet transfusion, coagulation factor infusion, recombinant factor therapy, interleukin and cytokine treatment.

The term "blood component" in this invention can mean any protein and non-protein component extracted from blood, or a product manufactured in vitro as a molecule or as a recombinant product based on the gene or genes known to code for the naturally-made blood component. It can include cellular and non-cellular components of blood.

Examples in this application include patients exposed to radiation. It is to be understood that the beneficial effects of the present invention is not limited to irradiated patients, but will include people exposed to thermal burns (external and internal), radiation burns, viral infections that cause bleeding, or people suffering from cancer, chemotherapy, and all kinds of procedures requiring transfusion of different kinds of blood cells to increase cell counts, such as patients who are septic or undergoing disseminated intravascular coagulation (DIC), thrombotic or hemorrhagic episodes, idiopathic (or immunological) thrombocytopenic purpura (ITP) or surgical patients.

Part of the information disclosed in this application was filed with the USPTO as a provisional application, No. 61/281,466 ("Submicron Particles for the Treatment of Radiation Damage in Patients") and as a non-provisional application, filed Nov. 16, 2010, USPTO Ser. No. 12/927,543, revealing an early date of invention. The entire disclosures of these prior applications are incorporated herein by reference.

Therefore, a need exists for new and improved submicron particles to decrease transfusion that can be used for treatment to decrease the need for transfusion such as red blood cell and platelet transfusion in human and animal patients. In this regard, the present invention substantially fulfills this need. In this respect, the submicron particles to decrease transfusion according to the present invention substantially departs from the conventional concepts and designs of the prior art, and in doing so provides an apparatus primarily developed for the purpose of treating to decrease the need for transfusion such as red blood cell and platelet transfusion in human and animal patients.

SUMMARY OF THE INVENTION

In view of the foregoing disadvantages inherent in the known types of treatment methods now present in the prior art, the present invention provides improved submicron particles to decrease transfusion, and overcomes the above-mentioned disadvantages and drawbacks of the prior art. As such, the general purpose of the present invention, which will be described subsequently in greater detail, is to provide new and improved submicron particles to decrease transfusion and method which has all the advantages of the prior art mentioned heretofore and many novel features that result in submicron particles to decrease transfusion which is not anticipated, rendered obvious, suggested, or even implied by the prior art, either alone or in any combination thereof.

To attain this, the present invention essentially comprises a new treatment of patients who need blood component treatment. A method to treat a patient who needs blood component transfusion comprised of the administration of submicron protein spheres where the size of the spheres range from one micron to less than 0.1 micron, and where the molecular weight of the spheres range from 780 billion Daltons to less than 0.8 billion Daltons. The protein spheres are suitable for administration to a patient intravenously, and the protein spheres having no biologically active molecule added or bound to them prior to patient administration.

By the intravenous administration of a novel product, which is a suspension of submicron-sized protein spheres, the patients will have less need of blood component infusions, as reflected in fewer episodes of transfusions or smaller quantities of transfused material each time or during the entire period of ill-health. The frequency of administration of the novel product can be daily, or less frequently, including up to once-every-5 days. The novel product is well tolerated. Medical, surgical and trauma patients will benefit.

Even still another object of the present invention is to provide a suspension of protein spheres that are essentially all smaller than one micron in diameter, with less than 1% of the spheres at or larger than one micron. The preferred protein source is human serum albumin. The spheres are made from soluble proteins in a process without the need to add surfactants or detergents, which is in contrast to the commonly owned prior art. The spheres can bind other molecules directly and spontaneously when they come into contact with other biologically active molecules including at least one coagulation factor (including fibrinogen); whether the at least one coagulation factor is supplied as a purified source, or as plasma outside the body, or as plasma inside the body of the patient. The spheres can possibly absorb cytokines in vivo and calm the cytokine storm caused by radiation.

There has thus been outlined, rather broadly, the more important features of the invention in order that the detailed description thereof that follows may be better understood and in order that the present contribution to the art may be better appreciated.

The invention may also include a method to treat a patient who needs blood component transfusion where said blood component includes red cells, white cells, platelets and plasma components.

In addition, among subjects exposed to an LD70 dose of gamma radiation survival is improved from 30% to 70% by administration of the product alone, without concomitant blood component support. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide new and improved submicron particles to decrease transfusion that has all of the advantages of the prior art treatment methods and none of the disadvantages.

It is another object of the present invention to provide new and improved submicron particles to decrease transfusion that may be easily and efficiently manufactured and marketed.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

DETAILED DESCRIPTION OF THE INVENTION

Although specific embodiments of the present invention will now be described, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the claims or appended claims.

Experiment One

Manufacture of Submicron Particles Small Enough to Remain in suspension for Over a Year in Room Temperature Purpose:
To disclose a method of mass-production of a suspension of particles that are essentially spherical and with a median diameter of less than one micron, manufactured from a high concentration of animal albumin.
Material and Method:
Bovine serum albumin powder was purchased from Boval Company LP, Cleburne, Tex. and dissolved in water to result in an 18% solution. The solution will be further processed as follows without the addition of surfactants or detergents. Glutaraldehyde solution was purchased from Sigma-Aldrich, St. Louis, Mo. 63103 and diluted to 0.15 mg per ml with water. A mixture of alcohol to be called EG was prepared as follows: 2850 ml of 100% ethanol USP grade was mixed with 950 ml of water, after which 7.6 ml of a glutaraldehye solution (25%) and 114 ml of a sodium chloride solution (0.9%, USP) was added to result in 3921.6 ml of EG solution. Sorbitol powder USP grade was purchased from Sigma-Aldrich and dissolved in water to form a 25% solution. Sodium caprylate was purchased from Jost Chemical Co., St. Louis, Mo. 63114 and dissolved in water to form a 10% solution.

The following steps were done at room temperature, 19° C. to 24° C. under sterile conditions. All the solutions were filtered via 0.2 micron filters before mixing in a class-100 clean room. At time zero, 190 ml of glutaraldehyde solution (0.15 mg/ml) was added to 381 ml of bovine serum albumin solution (18%) and well mixed in the container. Within 3 minutes, 3426 ml of EG was added and well mixed, at which time the solution turned turbid indicating the formation of spheres.

After one hour, the suspension was dialyzed in distilled water to remove the EG. After measuring the concentration of the spheres in the dialyzed suspension, sorbitol, caprylate and an additional aliquot of distilled water were added to the dialyzed suspension to result in a final concentration, respectively, of 5% sorbitol, 13.3 mg of caprylate per gram of total protein, and 8 mg of spheres/ml of suspension.

The suspension was subsequently filled into sterile containers, capped and sealed. Then the product was terminally sterilized by heating the suspension inside the container to 60° C. for 10 hours, or pressurized up to 600 MPa.
Results:
Analysis of the suspension showed that the particles are spherical and the median diameter was about 0.35 micron, with less than 1% of the sphere with diameter greater than one micron. No aggregates were observed. The suspension was stable after one year of storage in room temperature without constant agitation to keep the particles in suspension. There was no significant shift of size distribution of particles after one year of storage in room temperature.

The suspension was frozen and kept frozen at minus 18° C. for at least one year. Then samples were thawed and stored at room temperature for at least one year. Analysis of the size distribution of particles showed no significant change from the size distribution of particles in suspensions analyzed within days of completion of synthesis and terminal sterilization.

The density of the spheres is between 1.0 and 1.1 relative density since they do not settle to the bottom during prolong storage but are kept in suspension by the Brownian movement of the supernatant. Measurement of the size and molecular weight of the spheres showed that spheres with diameter of 1 micron and 0.1 micron have molecular weight of $780 \times 10^9$ Daltons and $0.78 \times 10^9$ Daltons, respectively. The same can be written as 780E+9 and 0.78E+9, respectively. The one micron spheres have a weight of about $128 \times 10^{-14}$ gram per sphere. The 0.1 micron spheres have a weight of about $0.13 \times 10^{-14}$ gram per sphere.
Comments:
Although bovine albumin solutions are used in this experiment, it is anticipated a number of other albumin solutions can be used, including human serum albumin (dialyzed in distilled water, or not dialyzed), other natural (human or animal) albumin or albumin molecules produced by recombinant-DNA methods. In addition, other proteins may be used to produce spheres with comparable functionality, including fibrinogen, immunoglobulin, collagen, gelatin, as disclosed in commonly owned U.S. Pat. No. 5,069,936 by Yen.

Although the spheres are not further coated with any other biologically active molecules during the manufacturing process in this experiment, it is anticipated that a number of other biologically active molecules, including coagulation factors, such as fibrinogen, von Willebrand factor, Factor IX and other coagulation factors may be added to the spheres during the manufacturing process. It is expected that various ratios of mixing of the biologically active molecule solution with the sphere suspension are permissible. Specifically, experiments have been conducted where, for example, a solution of fibrinogen up to 3 mg/ml may be mixed at a ratio of 1 part (by volume) of the fibrinogen solution to 4 parts (by volume) of the sphere suspension (the turbid suspension after addition of EG, and before dialysis of the EG-containing suspension with distilled water) to result in "coated spheres." See commonly owned international patent application number PCT/US2008/006014 by Yen.

Although a specific concentration of ingredient solutions are mentioned here as an example, other higher or lower concentrations can be used when combined with a compatible compensating concentration of other ingredients. For example, albumin solutions can vary between 5% to 20% in initial concentration before the addition of a glutaraldehyde solution, which can vary from 0.05 to 0.5 mg/ml. The concentration of ethanol in the EG mix can vary from 55% to 100%, while the glutaraldehyde concentration in EG can vary from 0.1 mg to 0.75 mg/ml and the sodium chloride concentration can vary from 0.5 to 0.005 mg/ml in the EG mix.

It is surprising that a suspension of protein sphere can undergo heating at 60 degree Centigrade for 10 hours without forming aggregates or clumps. The addition of sorbitol together with caprylate probably has a synergistic effect on protecting the protein spheres from aggregation or expression of new antigenic sites during the process of heating and subsequent cooling to room temperature.

Experiment Two

Submicron Protein Spheres Decreased Need for Platelet Transfusion and Red Cell Transfusion in Medium-Sized Animals Irradiated with a Potentially Lethal Dose of Gamma Radiation Purpose:
To find out if the administration of fibrinogen-coated albumin spheres (FAS) can decrease the need for blood component transfusions in irradiated medium-sized animals.
Materials and Methods:
FAS were manufactured with human serum albumin, coated with human fibrinogen molecules, and subjected to a terminal sterilization step essentially as described in Experiment One. The median diameter of the spheres in the suspension was about 0.4 micron. Less than 1% of the spheres had diameters larger than one micron. Institutional approval was obtained for this work using the medium-sized animals (median weight about 10 kg.) The animals were irradiated with 3 Gy of total body irradiation on day-zero. The irradiated animals were divided into two groups of equal numbers; the treatment group received a daily intravenous infusion of FAS (8 mg/kg) starting on the day when the platelet count dropped below 20,000/uL. FAS treatment was stopped when the animal's platelet counts recovered to above 20,000/uL. The control group received a daily intravenous infusion of normal saline (NS, 1 ml/kg) on the same days that the treatment group gets the FAS. Supportive care including antibiotics was provided as per institutional protocol. Bleeding Times were done using the buccal mucosal bleeding time method.
Results:
In this animal model, the platelet count (PLT) in non-irradiated animals was about 200,000/uL and the absolute neutrophil count (ANC) was about 2000/uL. All the irradiated animals showed significant decreases in PLT starting on day-6 and had PLT below 20,000/uL by day-11. The PLT from day-13 to day-17 was typically below detection (less than 1000/uL.) PLT recovery above 20,000/uL typically started on or after day-20. ANC typically dropped to zero by day-16 and started to recover only after day-20.

Bleeding Times were measured on the day when PLT dropped below 20,000/uL and prior to the first dose of FAS or NS treatment, and found to be abnormal (greater than 20 minutes) in all irradiated animals. Bleeding times measured 24 hours after the first dose of FAS treatment showed improvement to less than 13 minutes. Bleeding times in the control group continued to be abnormally high from day-11 to day-20. On several occasions, the animals showed petechiae, for which the animals were given an extra dose of treatment (i.e. 16 mg of FAS/kg on that day for the FAS group, or 2 ml/kg of NS in the control group.) In the FAS group, all the petechiae resolved within one day. Petechiae in the animals in the control group were resolved only after whole blood transfusion was given when the animals showed other clinical bleedings.

The animals in the FAS treatment group showed no clinical signs of adverse effects from FAS administration. Remarkably, none of the animals treated with FAS required any transfusion of platelets. One animal in the FAS group was given one transfusion of red blood cells (washed multiple times with saline to remove any residual platelets from the donor animal) per institutional protocol due to anemia: the animal showed no distress or any clinical signs of bleeding. Of particular interest was, one animal in the FAS group went into heat during the experiment and showed a normal amount of menstrual bleeding.

In contrast, the control group had an average of 3.2 episodes of clinical bleeding per animal during the 30 days of observation, for which they received an average of 3.5 episodes of whole blood transfusion (because in this animal model, platelet suspensions were not available.) Because of the whole blood transfusions, all the animals in the control group survived.
Comments:
The extremely low PLT and ANC showed that the radiation dose in this animal model was a lethal dose; all the animals in the control group survived only because of the excellent care provided to these animals, including the timely transfusion of whole blood. It is unfortunate from the scientific point of view that in this animal model, platelet suspensions were not available. Therefore the extremely thrombocytopenic animals did not receive only platelet transfusions—they also had red blood cells and plasma transfusions, which did not allow the investigator to study the effect of transfusing only platelets. However, the concomitant transfusion of red blood cells and plasma was probably medically beneficial to these animals in helping them recover faster.

The appearance of petechiae in these irradiated animals confirmed that they were extremely thrombocytopenic. It is remarkable that treatment with FAS can result in the resolution of petechaie. There is no product on the market that can achieve this result, except for platelet transfusion or after spontaneous recovery of the bone marrow to produce endogenous platelets. We gave those animals a double dose of FAS to prevent a potential worsening of their petechiae condition. More work needs to be done to see if they really need a double dose of FAS; or whether a daily dose of 8 mg FAS/kg is enough to control the situation anyway. More work needs to be done to see if daily doses less than 8 mg FAS/kg is still effective; or a daily dose of greater than 8 mg/kg is even more effective. Pharmacological studies have suggested that FAS have a long in vivo half-life: the dosing regimen may still be effective when given less frequently than a daily dose.

The spheres used in this experiment were coated with fibrinogen. It is expected that uncoated (blank) spheres (i.e. not coated with any coagulation factor during the manufacturing process) may work as well in similarly irradiated animals.

The data showed that in irradiated animals, submicron protein spheres can:
(a) reduce the need for platelet transfusion;
(b) reduce the need for red blood cell transfusions;
(c) reduce the incidence of internal bleeding (e.g. petechiae);
(d) reduce the incidence of major clinical bleeding (excessive menstrual bleeding); and
(e) improve bleeding time.

The reduction of about 3 episodes of clinical bleeding per animal (over the critical period) to zero episodes was highly significant and would allow the blood components to be reserved for use in other more-critically injured patients.

The institutional guidelines precluded the withholding of red blood cells or whole blood transfusions when an irradiated animal bleeds because it is known that it will bleed to death in the absence of transfusions. The data here suggest that FAS can improve survival of animals exposed to lethal doses of irradiation, particularly in a scenario where blood components are not available or cannot be given in time to the patient.

Experiment Three

Improvement in Survival Rate by Treatment with Submicron Particles in Mice Irradiated with a Lethal Dose of Ionizing Radiation Purpose:
To find out if submicron particles administered less frequently than a daily dosing regimen can improve the survival rate of mice exposed to a lethal dose of gamma radiation.
Material and Method:
FAS used in this experiment were similar to those used in Experiment Two. Mice were irradiated on day-zero with gamma radiation known to cause a mortality rate of 70% (LD70.) Test and control articles were administered intravenously to animals via the tail vein, at 24 hours, day-5 and day-10 after irradiation. Survival rate was scored on day-30.
Results:
There were 3 groups of mice (10 animals per group): (1) irradiated mice treated with normal saline (1 ml/kg, i.v.); (2) irradiated mice treated with submicron particles (8 mg/kg, equal to 1 ml/kg, i.v.); (3) mice not irradiated but treated with submicron particles (8 mg/kg). The results showed that all the animals in group (3) survived to the end of the experiment with no clinical signs or ill effect, when they were sacrificed. The survival rate of mice in group (1) and group (2) was 30% and 70%, respectively. The improvement in survival was statistically highly significant ($P<0.01$).

The experiment was repeated with irradiation at LD90. Survival rate in group (1) and group (2) was 10% and greater than 15%, respectively.
Comments:
Submicron particles administered intravenously at 8 mg/kg to animals exposed to lethal doses of ionizing radiation improved their survival rate. More experiments need to be done to see if a lower or higher dose of the particles will provide similar or better results.

Additional safety studies in healthy (non-irradiated) mice showed that three doses of FAS, each at 32 mg/kg, administered retroorbitally on day-0, day-5 and day-10 was safe: no clinical adverse effects were seen. The retroorbital approach was used to assure that the dosing amount was accurate. Using the tail vein repeatedly can lead to underdosing because of injuries to the tail vein which would have converted the intravenous attempts into intramuscular injections.

More tests need to be done to evaluate the effect of:
(a) a higher or lower FAS dose than 8 mg/kg;
(b) changing the "3 doses" to more doses or fewer doses;
(c) varying the interval between dosing (e.g. less than 5 days in between, or increasing to more than 5 days in between); and
(d) the best day to give the first dose (whether it is more efficacious to give the first dose before the day of irradiation, close to the day of irradiation, closer to a day when platelet count is the lowest, or even after the day when platelet count is the lowest.)

Although this experiment used submicron particles already coated with fibrinogen, it is anticipated that blank submicron particles not coated with any biologically active molecule during the synthesis steps may be equally effective, or even better.

The exact mechanism of protection leading to improved survival and less morbidity among survivors needs more study. Given the complexity of radiation damage, it is expected that there are multiple mechanisms each contributing in some way toward a combined and enhanced damaging effect. Therefore FAS may cause improved survival by breaking the chain of damaging reactions in the body, e.g. by calming the cytokine storm or other reactions after irradiation. It is expected that other products produced in a manner different from the present disclosure may be also effective in achieving the same end of improving survival after a massive dose of radiation. For example, products that have undergone the following steps may also be effective in improving survival (via mechanisms different or similar to those exerted by the presently-disclosed invention): the steps may involve the addition of surfactants or detergents, mixing with an emulsifier, spray drying, exposure to air/liquid interface stress, heat-fixation to render the particles stable against resolubilization in vitro or in vivo. In addition, particles that may not be essentially spherical in shape, particles with median diameters not less than one micron, suspensions with more than 1% of the particles being larger than one micron; they all may also be effective. Particles containing air and particles that exert their biological effects with a requirement to bind additional biological molecules through free functional groups such as amine, hydroxyl, carboxyl or sulfhydryl groups may also be effective in improving survival.

Although Experiment Two and Three described animals exposed to irradiation, the data reveal that submicron protein spheres of the present invention can be medically useful in medical, surgical, and trauma patients who need blood component treatment. The present invention does not involve molecules that stimulate blood cell production. The present invention is not a growth factor; it does not require the body to have sufficient number of progenitor cells which are to be stimulated. The present invention works immediately and is unlike stimulant molecules that need several days before the body can produce enough of its own blood cells (red blood cells, white blood cells or platelets) to affect clinical bleeding.

Ethical treatment of animals does not allow the use of animals larger than mice or rats to be used in large numbers for the study of the effect of transfusion in animals exposed to a variety of radiation doses, including LD90. Published data have shown that in large animals, transfusion of blood products and other medicine (listed in the Prior Art section) can improve survival. The data here, however, suggest that administration of the present invention will improve survival, with or without the use of other blood components or other medications. The data also suggest that the use of the present invention will decrease the need to use blood components or other medications, in irradiated patients and in patients with other medical and surgical needs.

It is well known that a variety of factors can affect susceptibility to radiation and chemotherapy. Genetic factors such as the strain in mice, age, and co-morbidity can convert an otherwise sublethal dose of radiation into a lethal dose. Patients on anti-platelet medication and/or anticoagulation medication can stop their medication for foreseeable events such as scheduled surgery. However, in the event of unforeseeable events, such as a nuclear event, the patient will still be under the effect of the medication. Additional experiments in mice have shown that mice irradiated with an otherwise sublethal dose of radiation (zero mortality) will suffer a mortality rate of about 70% to 90% if the mice are under anti-platelet treatment, such as by injection of anti-CD41 antibodies (an anti-platelet antibody.) However, when similarly treated mice (radiation plus anti-CD41) were infused with fibrinogen-coated submicron albumin spheres (8 mg/kg) on day 1, 5 10 (after radiation on day zero) the mortality rate decreased to about 10%. We expect similar results with patients who are under treatment with other anti-platelet medication and/or anti-coagulation medications. The mechanism of improved survival appears to be the effect of the present invention leading to a less leaky vascular system, resulting in a less severe loss of blood cells in terms of rate or concentration (including red blood cells, white blood cells, platelets) from the intravascular compartment. It is also observed that the recovery of cell counts (red blood cells, white blood cells, platelets) is more rapid in the recovery phase; possibly due to less leaky endothelial linings. We cannot rule out from the limited data in the experiment whether the present invention may affect positively the recovery of the bone marrow so that it can more readily generate new blood cells. We expect similar beneficial effects in less drastic situations: e.g. in lower doses of radiation where the mortality is not as high as 70% to 90%, but lower than 70%: in such situations, the patient can still benefit from the present invention by having even less severe morbidity and/or mortality due to the administration of the submicron particles of the present invention.

The fibrinogen content of the spheres used in Experiment Two and Three were found to be about 50 microgram of fibrinogen per mg sphere. New batches of spheres were made using lower concentrations of fibrinogen, resulting in spheres with about 20, 10, 5, and zero microgram of fibrinogen per mg spheres, respectively. All the above preparations of fibrinogen-containing spheres and the no-fibrinogen spheres (blank spheres) were effective in improving the survival of mice after exposure to lethal doses of irradiation. It is expected that in a large-animal model, less blood component transfusion will be needed to improve survival compared to similarly treated animals not administered the present invention of protein spheres with or without fibrinogen attached prior to administration to the patient.

The present invention is a suspension of protein spheres that are essentially all smaller than one micron in diameter, with less than 1% of the spheres at or larger than one micron. The preferred protein source is human serum albumin. The spheres are made from soluble proteins in a process without the need to add surfactants or detergents; in contrast to the prior art. The spheres can bind other molecules directly and spontaneously when they come into contact with other biologically active molecules including at least one coagulation factor (including fibrinogen); whether the at least one coagulation factor is supplied as a purified source, or as plasma outside the body, or as plasma inside the body of the patient. The spheres can possibly absorb cytokines in vivo and calm the cytokine storm caused by radiation.

There may be multiple mechanisms with which the present invention exerts its beneficial effects. The spheres may directly or indirectly improve the condition of the endothelium, or they may form co-aggregates with activated platelets to form effective plugs quickly to stem internal bleeding. Less bleeding allows the patient to divert needed energy towards the healing of other vital systems, resulting in improved survival.

The spheres of the present invention can be administered to patients before the time of irradiation, such as cancer patients scheduled to undergo radiation therapy. At the time the patient is not yet thrombocytopenic. This is in contrast to the use of spheres in the prior arts including those disclosed by Yen and other scientists, where spheres were always administered after the time of irradiation. Alternatively, the present invention can also be administered to patients after the exposure to radiation, such as after a nuclear event where the health problem of the patient is more than thrombocytopenia. At this time the patient will have multiple problems such as skin burn, shock, nausea, vomiting, hair loss, gastrointestinal symptoms, neurological symptoms, fever, infections, weakness etc. A single dose may be effective when given at the most appropriate time before or after the time of radiation. However, multiple doses spaced with a suitable interval in between may have a longer effective duration of action.

The data revealed that the present invention has the following benefits:

(a) When used alone in patients who can benefit from blood component treatment (blood cells or soluble fractions from blood) the present invention can decrease the morbidity (e.g. nausea and vomiting, or weight loss) and mortality of the patient during the critical period. The critical period will vary depending on the injury to the patient, e.g. the 30 or more days after a potentially-lethal or actually-lethal dose of radiation, or the thrombocytopenic period after chemotherapy, or the period after bone marrow abrasion before the bone marrow can recover, or the period after a viral infection that can cause massive hemorrhage. The patient can be a medical, surgical, or trauma patient, or a healthy patient about to undergo procedures needing blood component treatment.

(b) The present invention may be administered before the critical period, during the critical period, or even after the conventionally-recognized critical period.

(c) When the present invention is given in conjunction with blood components or other medications, the present invention will improve the effectiveness of the blood components or medications given concomitantly to the patient.

(d) When the present invention is given to a patient in need of blood component treatment or other medical treatment, the present invention can reduce the amount of the blood component or other medical treatment (e.g. interleukin-6) that would usually be administered (according to conventionally-established protocol.) The reduced amount of blood component or other medical treatment may be reflected in fewer episodes of treatment or a smaller quantity of treatment material needed.

(e) The present invention, when given alone or after being administered in conjunction with other blood component treatment or other medical treatment can improve the condition of survivors after the critical period.

(f) The present invention is highly beneficial to patients who are under anti-platelet therapy and/or anti-coagulation therapy, resulting in less morbidity and/or mortality caused by agents such as irradiation and/or chemotherapy.

This invention is intended for use in treating patients who need blood component transfusions. Blood component means various cell components or non-cell components derived from blood such as plasma proteins (including clotting factors and growth factors) and whole plasma (e.g. fresh frozen plasma which has all the soluble proteins in whole blood.) The protein used to construct the spheres can be human serum albumin from natural sources or recombinant DNA-derived serum albumin, or other proteins such as gelatin or synthetic polypeptides. Due to the small size of the spheres, ranging from one micron (with molecular weight of 780 billion Daltons) down to less than one tenth of one micron (with molecular weight of less than 0.8 billion Daltons,) the spheres tend to travel close to the interior wall of the blood vessels favoring their participation in the formation of plugs with activated platelets leading to a timely seal-off of any wound or leaky areas in the wall of the blood vessels, resulting in reduced bleeding. The distinguishing feature of the spheres is that they may have no biologically active molecules such as fibrinogen or other clotting factors which are added or bound to them during the synthesis process prior to patient administration. It is a possibility that the spheres can bind the various clotting factors including fibrinogen after the spheres have entered the blood stream, binding the necessary additional biologically active molecules supplied in vivo from the patient's own blood.

The most common blood cells transfused to patients are red cells but the term transfusion can be applied to platelet transfusions and plasma transfusions also. In this patent application, the term transfusion includes the administration of plasma components also. In clinical practice, when a patient needs two or more units of red cell transfusions, the clinician will order at least one unit of platelet to be transfused as well. In addition, fresh frozen plasma (FFP) will be administered. Fresh frozen plasma means plasma derived from a donor that has been freshly frozen for storage, but the frozen material will be thawed before administration intravenously to a patient. The reason is when a patient loses a large volume of blood, the patent needs not only a large volume of packed red cells, the patient has lost also a large amount of platelets and plasma, which need to be replaced by transfusion. If whole fresh plasma is not available, the clinician will order "frozen plasma" or plasma components to be administered, e.g. FFP, Factor VIII concentrates, or fibrinogen concentrates. At the present time, there are no established protocols to purposely transfuse white cells. However, white cells are present in packed red cell units and platelet units. To the extent that the present invention can decrease red cell transfusion or platelet transfusion, the present invention is decreasing white cell transfusion. The present invention does not rule out the possibility that in the future, subpopulations of white cells beneficial to a subset of patients may be purposely transfused to the patients. It is expected that in such a situation, the present invention can decrease the need of such specialized white cell transfusion as well.

The beneficial effect of the administration of the present invention is that the blood vessels are less leaky, whatever the cause of the leakiness may be. This is due to the fact that the spheres are trapped to enlarge the mass of the plug wherever activated platelets are at work to plug up the leaky spots on the wall of the blood vessels. The expected result is that during the ill-health period, the patient will need less frequent transfusions, or a smaller quantity of blood component needs to be administered, or both. The benefit is not just cost-saving; but less chance of the transmission of infectious agents and fewer transfusion-related reactions. Even so, there is decrease in the morbidity or mortality of the patient by use of the present invention.

When a patient has less internal or external bleeding, there is less chance that he will become anemic. One the other hand, for a patient that is already anemic, use of the present invention may slow down the rate of red cell loss, giving the patient more time to recover before he reaches the critical point where he must have a red cell transfusion. Pancytopenia is a common result of cancer and radiation exposure. Hypovolemia is common after a massive blood loss from gun-shot wound or other trauma, where red cells must be transfused. When only red cells are available and transfused but not platelets, a patient will suffered from dilutional thrombocytopenia. The lack of a sufficient concentration of platelets in vivo resulting in prolong bleeding is called thrombocytopenia. In this patent application, we further define thrombocytopenia as numerical (such as less than 100,000 platelets per microliter of blood) and functional (such as any of the inherited syndromes involving glycoproteins of platelets). Patients who have developed refractoriness to platelet transfusion due to a history of platelet transfusion, or bone marrow failure (with or without risk factors) can benefit from the present invention. Cancer patients and patients under cancer treatment, or anti-platelet medication tend to bleed. Patients under anti-platelet regiments who need emergency surgeries or have an overdose; patients exposed to viral infections, suffering from thermal or radiation burn can also benefit from the present invention. Other situations such as the effects of irradiation, sepsis, disseminated intravascular coagulation can also benefit from the present invention. Additional conditions include idiopathic/immune thrombocytopenic purpura, petechiae, echymosis, joint bleeding, intracranial and intestinal bleeding.

Prophylactic use of the present invention in patients expected to suffer from the above mentioned list of conditions or sickness may decrease the severity of the condition or sickness. The present invention may be even more effective when used in a preventive way than after the sickness has occurred.

Although the administration of blank protein spheres (having no fibrinogen attached prior to administration to patient) of the present invention has been shown to be effective in reducing the bleeding time and in improving survival after lethal irradiations in animal models, such experiments cannot be duplicated in human volunteers due to ethical reasons. In view of the possibility that different human patients may have different concentrations of the variety of clotting factors in their blood, a product with some fibrinogen molecules already attached to the spheres may ensure effectiveness in a wide number of patients and situations. Experiments have shown that spheres containing less than 20 microgram of fibrinogen per milligram of spheres have medical benefits. Prior art produced spheres containing fibrinogen on the spheres but at higher concentrations than 20 microgram of fibrinogen per mg sphere. Blank spheres of a size larger than one micron are not effective in reducing bleeding time (as disclosed in the prior art) probably due to their travelling at a distance too far from the endothelium to be effective. Therefore to be effective in vivo, spheres of the prior art need to be pre-loaded with fibrinogen during the manufacturing process at a concentration higher than 20 microgram of fibrinogen per mg sphere.

While embodiments of the submicron particles to decrease transfusion have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method to treat a patient who needs blood component transfusion, said method comprising the steps of:
   a) producing a suspension of protein spheres comprising the steps of:
      preparing a mixture by mixing an albumin solution with a glutaraldehyde solution and an ethanol solution;
      removing said ethanol solution from said mixture; and
      adding sorbitol and sodium caprylate to said mixture; and
   b) administering intravenously said suspension of said protein spheres to a patient, said protein spheres having a size less than 1.0 micron, and wherein said protein spheres having a molecular weight less than 780 billion Daltons.

2. The method in accordance with claim 1, wherein said step of administering to the patient is to provide treatment to the patient needing blood component transfusion, wherein said blood component is at least one component selected from the group consisting of red cells, white cells, platelets, and plasma components.

3. The method in accordance with claim 1, wherein said step of administering to the patient is to provide treatment to the patient needing blood component transfusion, wherein said treatment reduces one of transfusion frequency, blood components transfusion quantity, and blood components transfusion frequency and quantity that will otherwise be needed to decrease morbidity or mortality of the patient.

4. The method in accordance with claim 1, wherein said step of administering to the patient is to provide treatment to the patient needing biologic molecules to stimulate one of red cell, white cell, platelet production, wherein said biologic molecules being one of synthetic biologic molecules, and recombinant biologic molecules and wherein said administration of said protein spheres decreases a use of said biological molecules.

5. The method in accordance with claim 1, wherein said step of administering to the patient is to provide treatment to the patient needing small mimetic molecules to stimulate one of red cell, white cell, and platelet production, and wherein said administration of said protein spheres decreases a use of said small mimetic molecules.

6. The method in accordance with claim 1 further comprising the step of providing a dosing schedule of one of a daily intravenous dosing, and at least five days in between doses.

7. The method in accordance with claim 1, wherein said step of administering to the patient intravenously further comprising of administration of said protein spheres by one of directly into a vein of the patient, and via an intravenous fluid line.

8. The method in accordance with claim 1, wherein said protein spheres administered to the patient are of at least 4 mg spheres per kilogram weight.

9. A method to treat a patient who needs blood component transfusion, said method comprising the steps of:
   a) producing a suspension of protein spheres comprising the steps of:
      preparing a mixture by mixing an albumin solution with a glutaraldehyde solution and an ethanol solution;
      adding or bounding fibrinogen molecules to said protein spheres, said fibrinogen molecule being at a concentration less than 20 microgram of fibrinogen per milligram of protein sphere;
      removing said ethanol solution from said mixture to prepare a pre-suspension; and
      adding sorbitol and sodium caprylate to said pre-suspension; and
   b) administering said suspension of said protein spheres to a patient, said protein spheres having a size less than 1.0 micron, and a molecular weight less than 780 billion Daltons, said protein spheres being configured for administration to the patient intravenously.

10. The method in accordance with claim 9, wherein said step of administering to the patient is to provide treatment to the patient needing blood component transfusion, wherein said blood component is at least one component selected from the group consisting of red cells, white cells, platelets, and plasma components.

11. The method in accordance with claim 9, wherein said step of administering to the patient is to provide treatment to the patient needing blood component transfusion, wherein said treatment reduces one of transfusion frequency, blood components transfusion quantity, and blood components transfusion frequency and quantity that will otherwise be needed to decrease morbidity or mortality of the patient.

12. The method in accordance with claim 9, wherein said step of administering to the patient is to provide treatment to the patient needing biologic molecules to stimulate one of red cell, white cell, platelet production, wherein said biologic molecules being one of synthetic biologic molecules, and recombinant biologic molecules and wherein said administration of said protein spheres decreases a use of said biological molecules.

13. The method in accordance with claim 9, wherein said step of administering to the patient is to provide treatment to the patient needing small mimetic molecules to stimulate one of red cell, white cell, and platelet production, and wherein said administration of said protein spheres decreases a use of said small mimetic molecules.

14. The method in accordance with claim 9 further comprising the step of providing a dosing schedule of one of a daily intravenous dosing, and at least five days in between doses.

15. The method in accordance with claim 9, wherein said step of administering to the patient intravenously further comprising of administration of said protein spheres by one of directly into a vein of the patient, and via an intravenous fluid line.

16. The method in accordance with claim 9, wherein said protein spheres administered to the patient are of at least 4 mg spheres per kilogram weight.

* * * * *